United States Patent
Rioux et al.

(10) Patent No.: US 8,608,734 B2
(45) Date of Patent: Dec. 17, 2013

(54) RF ABLATION PROBE ARRAY ADVANCING DEVICE

(75) Inventors: Robert F. Rioux, Ashland, MA (US); Jeffery V. Bean, Fitchburg, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1335 days.

(21) Appl. No.: 11/961,703

(22) Filed: Dec. 20, 2007

(65) Prior Publication Data

US 2008/0161804 A1    Jul. 3, 2008

Related U.S. Application Data

(60) Provisional application No. 60/882,128, filed on Dec. 27, 2006.

(51) Int. Cl.
*A61B 18/14*    (2006.01)

(52) U.S. Cl.
USPC ............... 606/41; 606/27; 606/28; 606/29; 607/101; 607/102

(58) Field of Classification Search
USPC ............... 606/27–50; 607/101–102
See application file for complete search history.

(56) References Cited

U.S. PATENT DOCUMENTS

| | | | |
|---|---|---|---|
| 5,868,740 A | 2/1999 | LeVeen et al. | |
| 5,967,984 A | 10/1999 | Chu et al. | |
| 6,379,353 B1 | 4/2002 | Nichols | |
| 6,468,273 B1 | 10/2002 | LeVeen et al. | |
| 6,716,195 B2 * | 4/2004 | Nolan et al. | 604/131 |
| 6,889,089 B2 | 5/2005 | Behl et al. | |
| 6,962,588 B2 * | 11/2005 | Sauvageau et al. | 606/41 |
| 2003/0069543 A1 * | 4/2003 | Carpenter et al. | 604/190 |
| 2003/0078572 A1 * | 4/2003 | Pearson et al. | 606/34 |
| 2004/0116849 A1 * | 6/2004 | Gardeski | 604/95.04 |
| 2004/0158239 A1 * | 8/2004 | Behl et al. | 606/41 |
| 2004/0225286 A1 * | 11/2004 | Elliott | 606/41 |
| 2005/0137659 A1 | 6/2005 | Garabedian et al. | |
| 2005/0283217 A1 * | 12/2005 | Wojciechowicz | 607/119 |
| 2006/0084965 A1 | 4/2006 | Young | |

FOREIGN PATENT DOCUMENTS

| | | |
|---|---|---|
| EP | 0 834 288 A1 | 4/1998 |
| WO | WO 96/29946 A1 | 10/1996 |
| WO | WO 2005/079689 A1 | 9/2005 |

OTHER PUBLICATIONS

European Office Communication dated Dec. 2, 2010 from the related European Application No. 07869688.7-2305, Applicant: Boston Scientific Limited (4 pages).

PCT International Preliminary Report on Patentability (Chapter I of the Patent Cooperation Treaty) for PCT/US2007/088430, Applicant: Boston Scientific Limited, Form PCT/IB/326 and 373, dated Jul. 9, 2009 (8 pages).

(Continued)

*Primary Examiner* — Michael Peffley
*Assistant Examiner* — Khadijeh Vahdat
(74) *Attorney, Agent, or Firm* — Bingham McCutchen LLP

(57) ABSTRACT

An array advancing device that attaches to a tissue ablation probe comprises a housing sized for receiving the handle and reciprocating plunger of the ablation probe, the housing having a proximal section configured to engage the plunger, and a distal section configured to engage the handle, the proximal housing section being controllably moveable relative to the distal housing section to thereby controllably move the plunger relative to the handle.

15 Claims, 8 Drawing Sheets

(56) References Cited

OTHER PUBLICATIONS

PCT International Search Report for PCT/US2007/088430, Applicant: Boston Scientific Scimed, Inc., Form PCT/ISA/210 and 220, dated Jun. 17, 2008 (6 pages).
PCT Written Opinion of the International Search Authority for PCT/US2007/088430, Applicant: Boston Scientific Scimed, Inc., Form PCT/ISA/237, dated Jun. 17, 2008 (6 pages).
European Office Communication dated Oct. 12, 2012 from the related European Application No. 07869688.7-2305, Applicant: Boston Scientific Limited (3 pages).
European Office Communication Regarding Result of Consulation by Telephone dated Nov. 8, 2012 from the related European Application No. 07869688.7-2305, Applicant: Boston Scientific Limited (3 pages).

* cited by examiner

RF ABLATION PROBE ARRAY ADVANCING DEVICE

RELATED APPLICATION DATA

The present application claims the benefit under 35 U.S.C. §119 to U.S. provisional patent application Ser. No. 60/882,128, filed Dec. 27, 2006. The foregoing application is hereby incorporated by reference into the present application in its entirety.

FIELD OF INVENTION

The present invention relates to systems and methods for ablating tissue in interior regions of the human body and, more particularly, to a device for more precise and controlled deployment of elongated electrode elements of an radio frequency (RF) electrode array probe.

BACKGROUND

The delivery of radio frequency (RF) energy to target regions of tissue is known for a variety of purposes of particular interest to the present invention. For example, U.S. Pat. Nos. 5,868,740, 6,379,353, 6,468,273, 6,889,089, U.S. Patent Application Publication No. 2005-0137659, and PCT application WO 96/29946 describe some of such tissue ablation systems.

The delivery of RF energy to target regions within tissue is used to treat maladies within the body. Thermal coagulation of tissue using RF energy may be delivered to diseased regions, e.g., tumors, for the purpose of ablating predictable volumes of tissue with minimal patient trauma. Physicians frequently make use of tissue piercing probes to gain access to interior regions of the body for this purpose. Such probes may carry an array of elongate (e.g., wire) electrode elements that are deployable from a distal end of the probe into the tissue region to be ablated.

One family of commercially available RF ablation probes are the LeVeen®Needle Electrode and the LeVeen CoAccess™-Electrode System (collectively referred to herein as the "LeVeen ablation probe"), manufactured and distributed by Boston Scientific Corporation. The LeVeen ablation probe comprises an array of elongate wire electrode elements that are deployable from a distal portion of an elongate delivery cannula. A handle is connected to a proximal portion of the delivery cannula, and a plunger is coupled in a reciprocating fashion to the handle. In particular, the plunger is fixedly coupled to the electrode array elements such that, when the plunger is extended proximally relative to the handle, the electrode elements are withdrawn into the cannula, and when the plunger is depressed distally into the handle, the electrode elements are deployed out of the cannula.

Depending on the size of the lesion and the size of the electrode elements needed to ablate the lesion, the attending physician may only deploy a portion of the electrodes to initiate the ablation procedure, and then deploy additional portions (i.e., lengths) of the electrode elements as the procedure continues. However, it may be difficult for the physician to precisely control and deploy the electrode elements using the plunger-handle arrangement. Thus, a need exists for controlling the deployment of elongate electrode elements from probes such as (but not just) the LeVeen ablation probe so the array elements are precisely deployed.

SUMMARY OF THE INVENTION

An array advancing device is provided for more precisely controlling deployment of one or more elongate electrode elements from an RF ablation probe, such as (but not limited to) a LeVeen ablation probe. In various embodiments, the array advancing device comprises a housing sized for receiving the handle and plunger of an RF ablation probe. The housing includes a proximal section configured to engage the plunger, and a distal section configured to engage the handle, the proximal housing section being controllably moveable relative to the distal housing section.

In one embodiment, the proximal housing section of the array advancing device is controllably movable relative to the distal housing section by rotating the proximal housing section relative to the distal housing section. The rotation of the proximal housing section relative to the distal housing section in a first direction depresses the plunger into the handle, and in a second direction extends the plunger proximally relative to the handle. The proximal housing section may comprise a protrusion extending radially inward and is sized to cooperatively engage a distal facing surface of the ablation probe plunger for causing the plunger to be extended proximally relative to the handle upon rotation of the of the proximal housing section in the second direction relative to the distal housing section. The inwardly extending protrusion of the proximal housing section comprises a flexible resilient material that depresses to allow the ablation probe plunger to be axially received through a distal end opening of the proximal housing section and is self-restoring to cooperatively engage the distal facing surface of the plunger when the plunger is positioned in the proximal housing section.

In one embodiment, the array advancing device comprises a drive mechanism that precisely controls movement of the proximal housing section relative to the distal housing section. The array advancing device may further comprise an actuator that precisely controls movement of the proximal housing section relative to the distal housing section.

In various embodiments, the proximal housing section may be fixedly or detachably coupled to the distal housing section. By way of non-limiting example, the proximal housing section may be threadably coupled to the distal housing section. By way of another, non-limiting example, the proximal housing section comprises a proximal end opening sized to receive the ablation probe therethrough, wherein a retention member may be secured over the proximal end opening of the proximal housing section. The distal housing section comprises respective proximal and distal openings and defining an interior chamber such that the ablation probe may be axially received through the proximal end opening, with the probe cannula extending through the distal end opening when the probe handle is seated in the chamber. In yet another embodiment, one or both the distal and the proximal housing sections of the array advancing device comprises a two-piece hinged assembly.

Other and further features and advantages of embodiments of the invention will become apparent from the following detailed description, when read in view of the accompanying figures.

BRIEF DESCRIPTION OF THE DRAWINGS

The drawings illustrate the design and utility of various embodiments of the invention, in which similar elements are referred to by common reference numerals, and in which.

DETAILED DESCRIPTION OF THE ILLUSTRATED EMBODIMENTS

Figure 1:
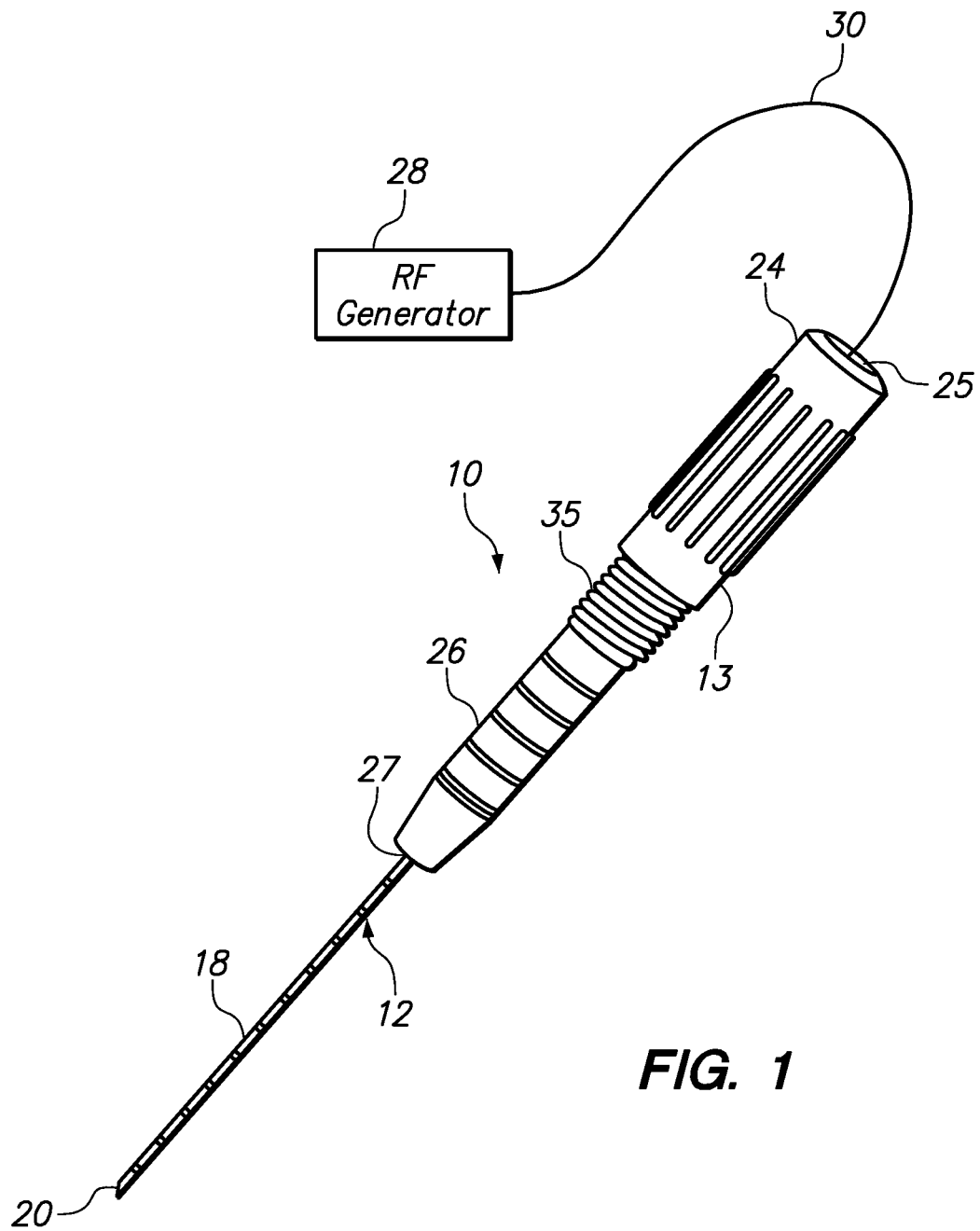
FIG. 1 is a side perspective view of an array advancing device constructed in accordance with one embodiment and carrying an RF ablation probe.

FIG. 1 depicts an array advancing device 10, constructed in accordance with one embodiment of the invention. The array advancing device 10 is attached to a tissue ablation probe 12 (best seen in FIGS. 2-4). The ablation probe 12 is connected via a RF cable 30 to a generator 28, which supplies RF energy to an array 22 of elongate electrode elements 41 (seen in FIGS. 3-4) that are deployable from a distal end opening 20 of a tissue-piercing delivery cannula 18 that extends distally from the probe 12.

Figure 2:
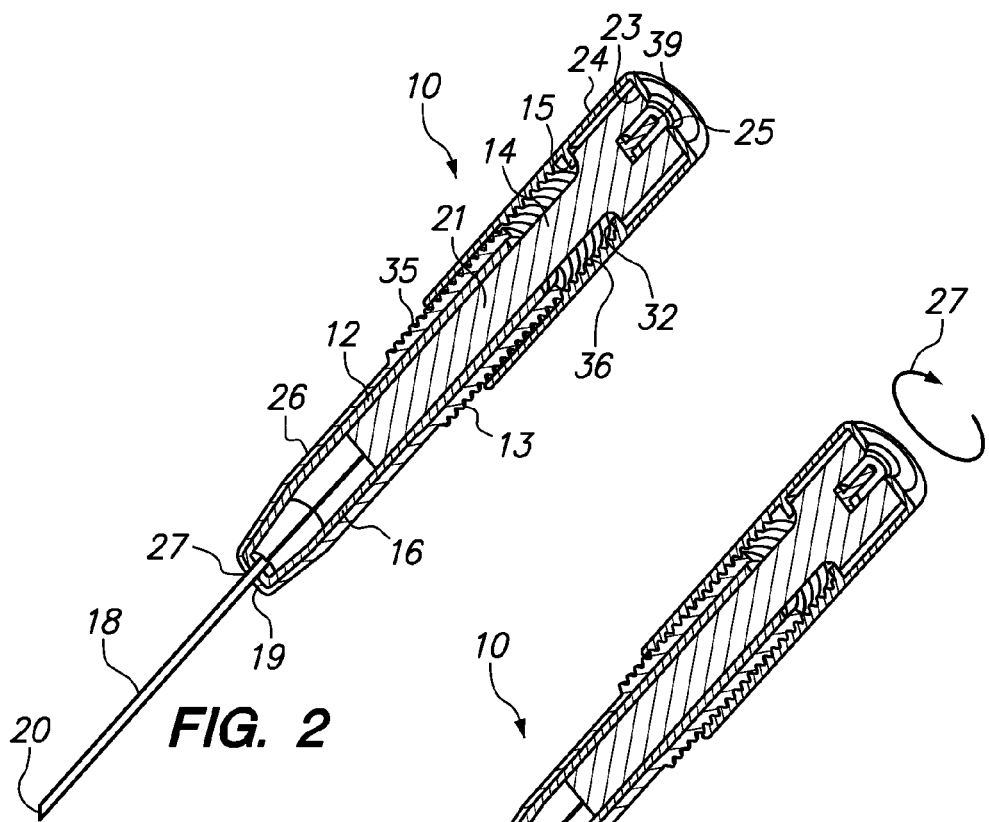
FIGS. 2-4 are cross-sectional views of the array advancing device and RF ablation probe of FIG. 1, with a distal end array of electrode elements depicted retracted into the probe cannula (FIG. 2); partially deployed from the probe cannula (FIG. 3); and fully deployed from the probe cannula (FIG. 4).

With reference also to FIG. 2, the array advancing device 10 comprises a generally cylindrical (i.e., barrel-shaped) housing 13 that defines an interior chamber 21 sized for receiving the ablation probe 12. The housing 13 includes a proximal housing section 24 that is threadably coupled and moveably relative to a distal housing section 26. The proximal housing section 24 includes a proximal end opening 25 sized to allow the RF cable 30 to be connected to a proximal end connector socket 39 of the ablation probe 12, when the probe 12 is seated in the housing chamber 21. The distal housing section 26 comprises a distal opening 27 sized to allow the delivery cannula 18 of the ablation probe 12 to extend there through.

Figure 3:
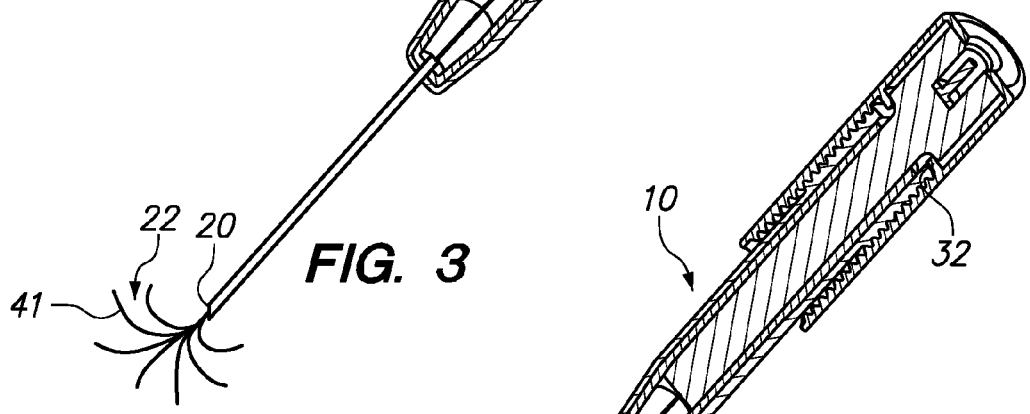
Figure 4:
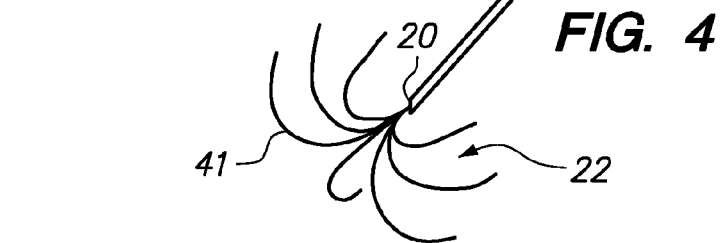

The ablation probe 12 generally includes a handle 16 connected to a proximal portion 19 of the delivery cannula 18, and a plunger 14 movable axially relative to, and seated in a proximal end of, the handle 16. An array 22 of elongated electrode array elements 41 is deployable from, and retractable into, a distal end portion 20 of the delivery cannula 18. In particular, the plunger 14 is movably coupled to the handle 16 and fixedly coupled to the electrode array elements 41, such that, when the plunger 14 is fully extended proximately relative to the handle 16, the electrode array elements 41 are completely withdrawn into the cannula 18 (illustrated in FIG. 2), and when the plunger 14 is fully depressed distally into the handle 16, the electrode array elements 41 are fully deployed out of the cannula 18 (illustrated in FIG. 4). FIG. 3 depicts the array 22 of electrode elements 41 partially deployed from the probe cannula 18, with the plunger 14 being positioned approximately in a middle of its range of movement relative to the handle 16.

In accordance with a general aspect of the invention, the proximal housing section 24 is configured to engage the plunger 14, and the distal housing section 26 is configured to engage the handle 16. Thus, because the proximal housing section 24 is controllably movable relative to the distal housing section 26 by rotating the proximal housing section 24 relative to the distal housing section 26, the plunger 14 of the ablation probe 12 seated in the housing chamber 21 is similarly controllably moveable axially relative to the handle 16. It will be appreciated that, by selecting a desired thread gauge (i.e., the axial distance between adjacent threads) for rotatably engaging the respective proximal and distal housing sections 24 and 26, the amount of linear movement of the plunger 14 relative to the handle 16, and thus deployment of the electrode array 22 out of (or into) the cannula 18, may be vary for the same amount of rotational movement of the respective housing sections 24 and 26. In this manner, the deployment of the electrode elements 41 of the array 22 into tissue may be much more precisely controlled by an attending physician, then when directly moving the plunger 14 relative to the handle 16.

More particularly, as the proximal housing section 24 is rotated relative to the distal housing section 26 in a first direction (indicated by arrow 27 in FIG. 3), the distal housing section 26 moves axially into the proximal housing section 24, and a portion 23 of the interior wall of the proximal housing section 24 engages and depresses the plunger 14 into the handle 16, thereby deploying the electrode array elements 41 out the distal end opening 20 of the delivery cannula 18. As the proximal housing section 24 is rotated in the opposite direction relative to the distal housing section 26 an annular protrusion 32 extending radially inward from the interior wall of the proximal housing 24 engages a distal facing surface 15 of the plunger 14, thereby pulling (extending) the plunger 14 out of the handle 16, and retracting the electrode elements 41 of the array 22 back into the distal end opening 20 of the cannula 18. Thus, the interior of the proximal housing section 26 and annular protrusion 32 are sized and configured to hold and move the plunger 14, as the proximal housing section 24 is rotated in either direction relative to the distal housing section 26.

Figure 10:
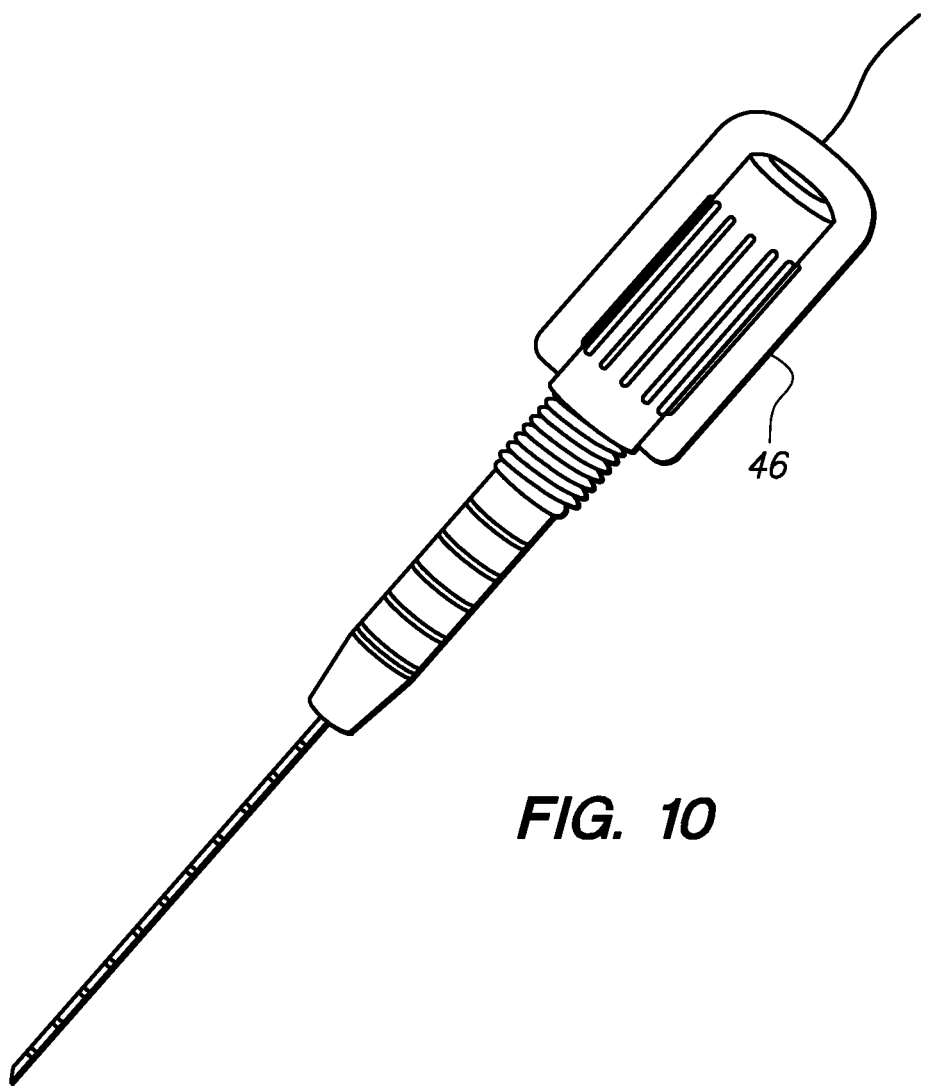
FIG. 10 is a perspective view of another embodiment of the array advancing device, depicting an actuator.

While the housing sections 24 and 26 of the array advancing device 10 may be manually rotated relative to one another, in alternate embodiments, a drive mechanism 46 that more precisely controls rotational movement of the proximal housing section 24 relative to the distal housing section 26 may be employed. By way of example, a drive mechanism 46 (e.g., a motor or other actuator) may be mounted on the proximal housing section 24 (depicted schematically in FIG. 10) to provide the relative rotational movement of the proximal housing section 24, while the attending physician grips the distal housing section 26.

As will be appreciated, while the threads 36 of the proximal housing section 24 are located on its interior wall, and the threads 35 of the distal housing section 26 are located on its exterior wall, the opposite configuration (i.e., proximal housing section threads 36 on its exterior wall and distal housing section threads 35 on its interior wall) will work equally well. Alternatively, the controlled relative movement of the housing sections 24 and 26 may be provided by direct linear (i.e., axial sliding) movement of the respective housing sections relative to one another (not shown).

Figure 5A:
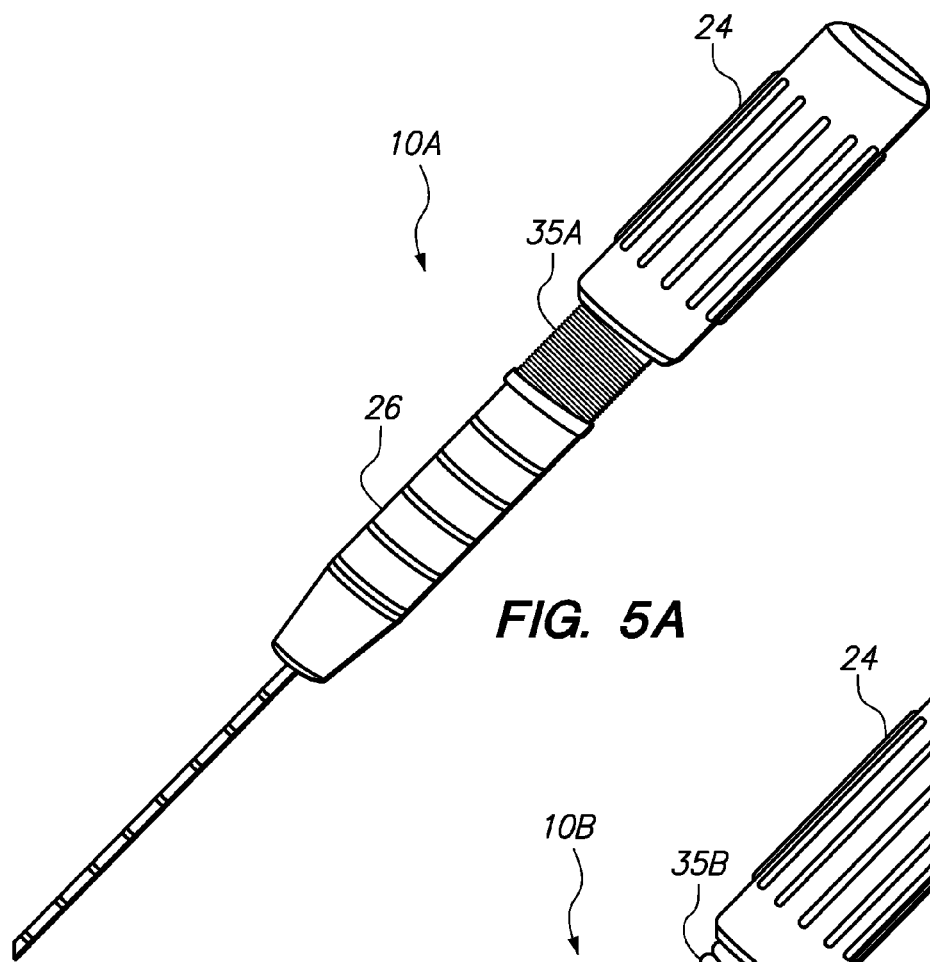
FIGS. 5A-B are side views of embodiments of the array advancing device having different thread pitches for correspondingly different linear array deployment rates.
Figure 5B:
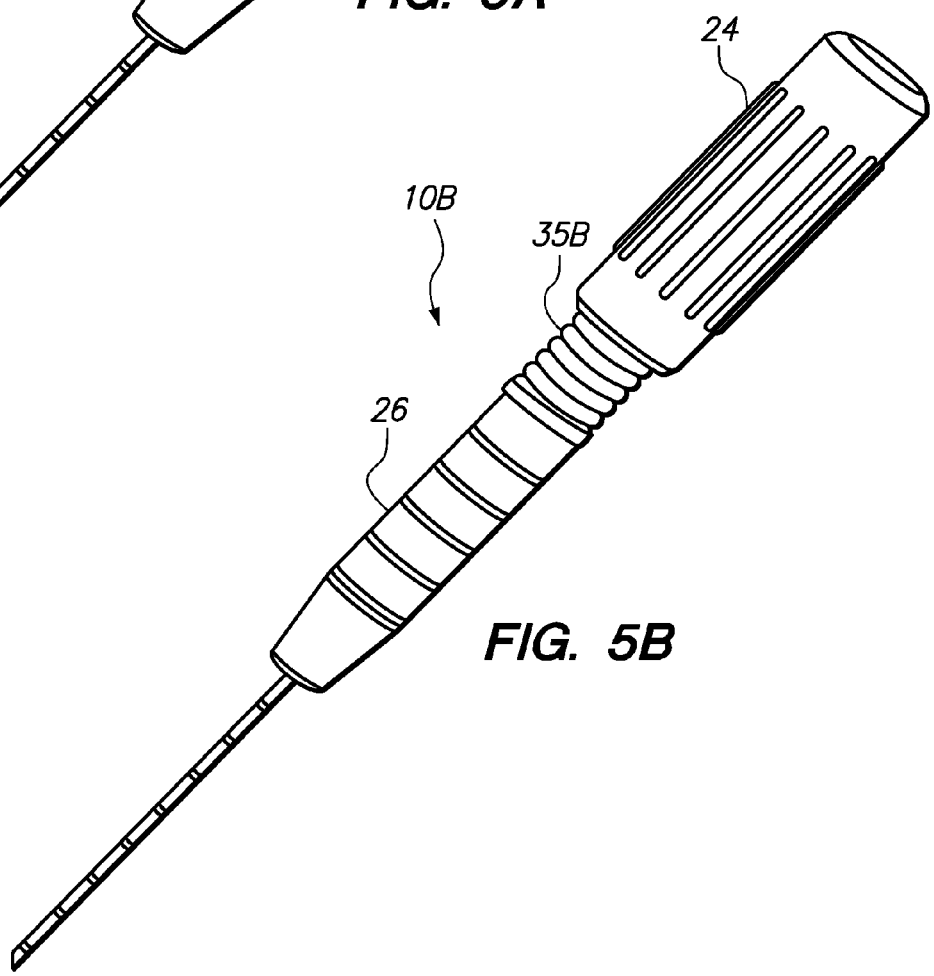

As noted above, the gauge of the threads 36 and 35 for rotatably coupling the respective proximal and distal housing sections 24 and 26 may be varied in order to correspondingly vary the amount of relative linear (axial) movement of the respective sections 24 and 26 corresponding to the amount of relative rotational movement. By way of brief illustration, FIGS. 5A and 5B depict variations of the array advancing device, referred to as 10A and 10B, respectively, in which the thread gauge of the exposed distal housing section threads, referred to as 35A and 35B, respectively, is either substantially less (i.e., with narrower threads for finer control) or substantially greater (i.e., with wider threads for less fine control, but more rapid electrode deployment) than the threads 35 of the device 10 of FIGS. 1-4.

Figure 6A:
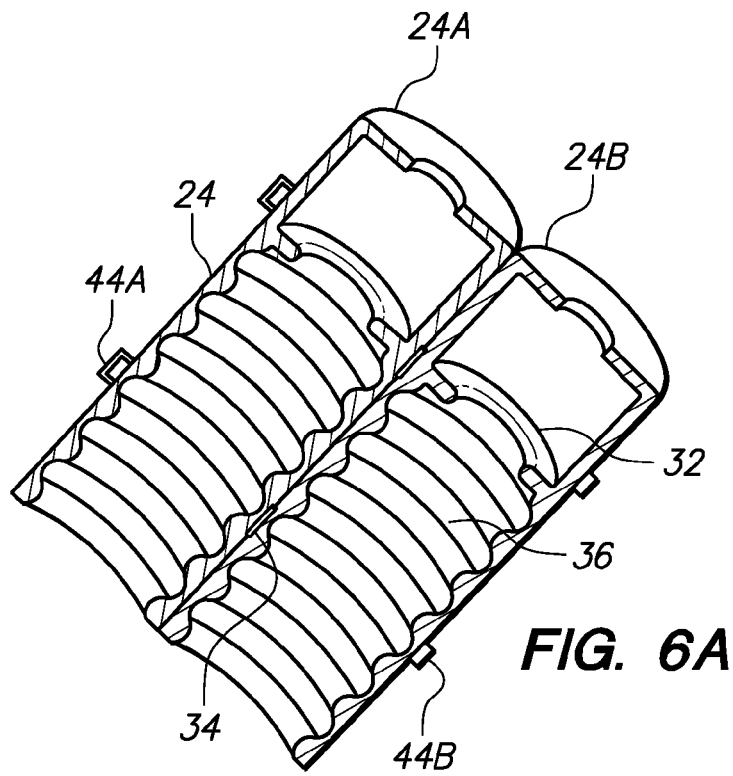
FIGS. 6A-B are cross-sectional views of an alternative embodiment of the array advancing device, depicting hinged assemblies having two adjacent open portions of the distal and proximal housing sections respectively.
Figure 6B:
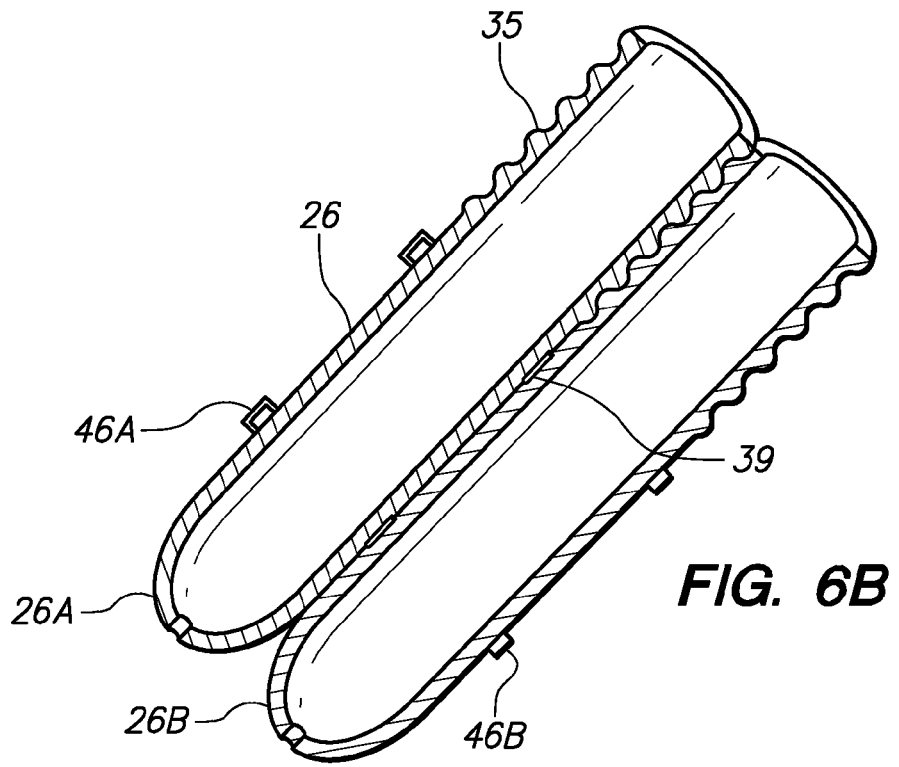

FIGS. 6A-B depict on embodiment of the array advancing device 10, in which the respective proximal and distal housing sections 24 and 26 are detachable from one another (e.g., by fully unscrewing the proximal section 24 from the distal section 26). As shown in FIG. 6A, the proximal housing section 24 comprises a two-piece hinged assembly having two adjacent open portions 24A and 24B joined by one or more hinges 34. The proximal housing portions 24A and 24B can be secured to each by one or more pairs of corresponding snap fittings 44A-44B. Similarly, as shown in FIG. 6B, the distal housing section 26 comprises a two-piece hinged assembly having two adjacent open portions 26A and 26B joined by one or more hinges 39. The distal housing portions 26A and 26B can be secured to each by one or more pairs of corresponding snap fittings 46A-46B. The respective hinged assemblies 24A-B and 26A-B allow for the proximal and distal housing sections to be separately attached around the respective plunger 14 and handle 16 of the ablation probe 12 (not shown in FIGS. 6A-B), after which the distal housing section 26 may be threadably engaged with (i.e., screwed into) the proximal housing section 24, along the respective threads 36 and 35.

Figure 7:
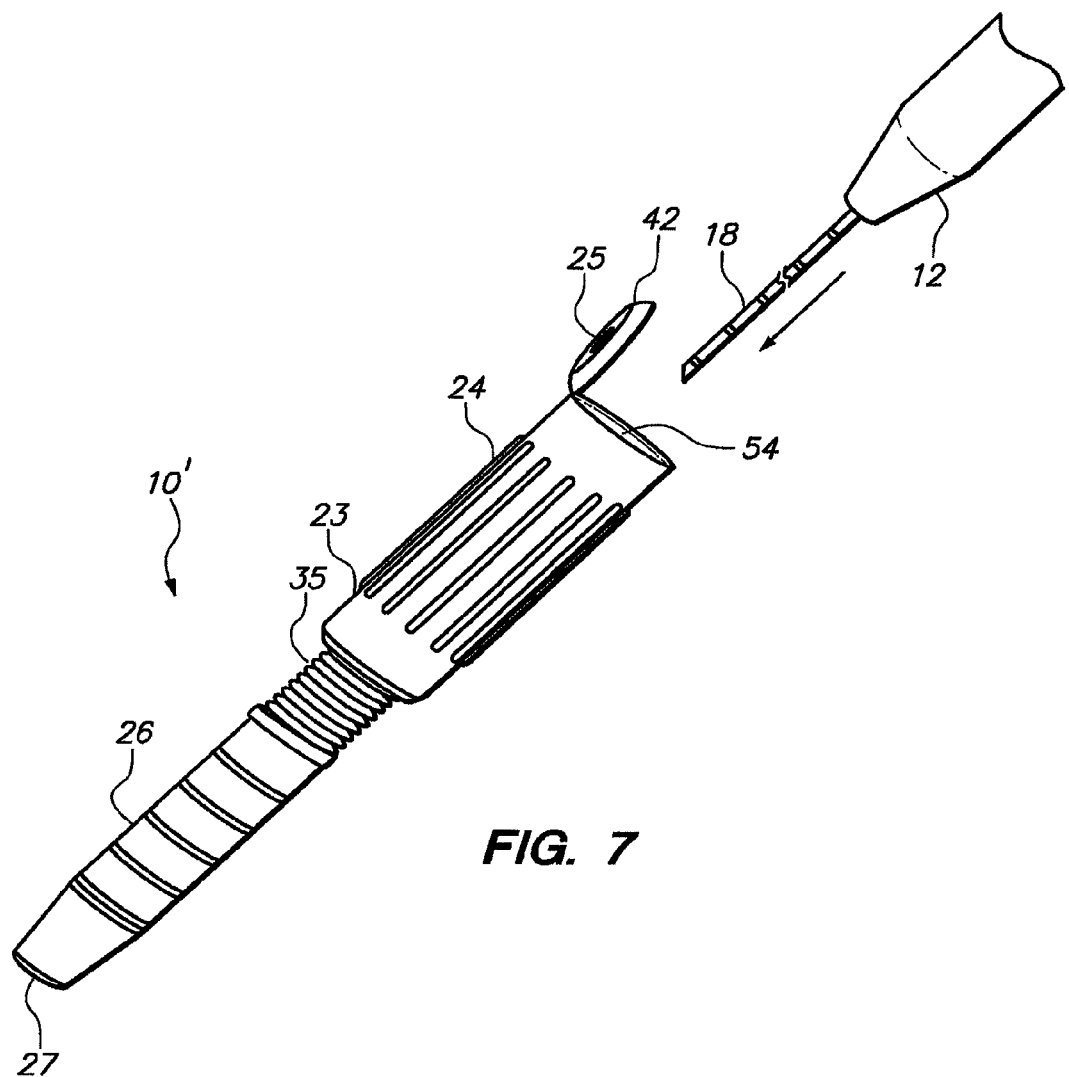
FIG. 7 is a perspective view of an alternative embodiment of the array advancing device, depicting a RF ablation probe being loaded into the device through a proximal end opening.

Alternately, with reference to FIG. 7, the proximal 24 and the distal 26 housing sections of the housing 23 of the array advancing device, referred to as 10', may be fixedly coupled together, with the proximal housing section 24 including a proximal end opening 54 sized to receive the ablation probe 12 axially loaded there through. A retention member 42 may be releasably-secured over the proximal end opening 54, e.g., after the ablation probe has been loaded into the array advancing device 10'. By way of example, the retention member 42 may be hingedly attached to the body of the proximal housing section 24, and includes the opening 25 for allowing the RF cable 30 to be connected to the ablation probe 12, as illustrated in FIGS. 1 and 2. The advancing array device 10' comprises a distal end opening 27 in the distal housing section 26 through which the ablation probe cannula 18 extends when the ablation probe 12 is axially loaded through the proximal end opening 54 and positioned in the proximal housing section 24. Once the ablation probe 12 is loaded into the chamber of the coupled housing sections 24 and 26, the retention member 42 is secured over the proximal end opening 54 of the proximal housing section 24 to secure the ablation probe 12 in the array advancing device 10'.

Figure 8:
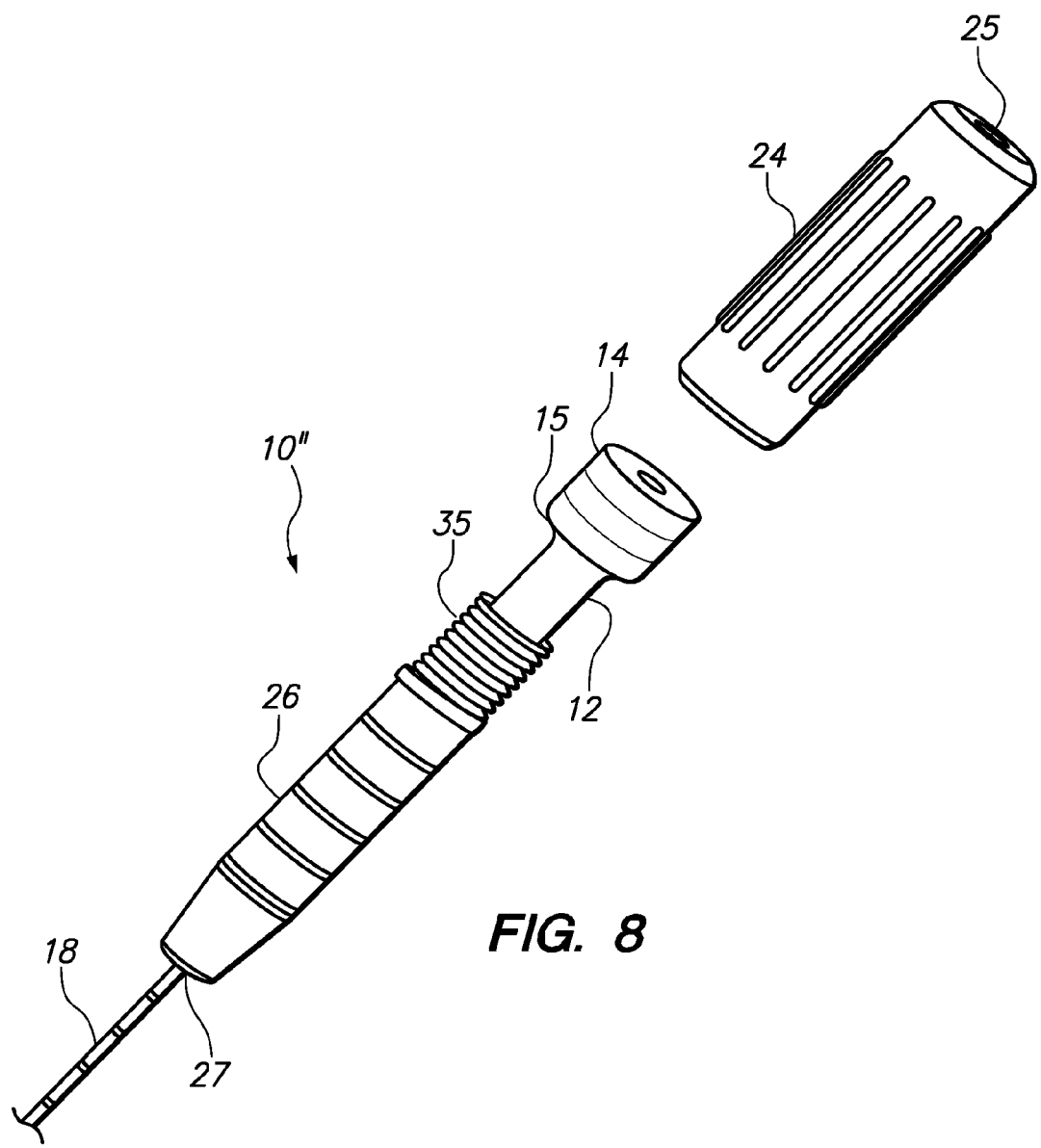
FIG. 8 is a perspective view of another alternative embodiment of the array advancing device, depicting an RF ablation probe loaded into the device, with a proximal housing piece removed.

Referring now to FIG. 8, in another embodiment of the array advancing device, referred to as 10'', the proximal and distal housing sections 24 and 26 are detachably coupled, allowing for axially loading the ablation probe 12 directly into the distal housing section 26, and then rotatably engaging (i.e., screwing on) the proximal hosing section 24 to the distal housing section 26, over the probe plunger 14, until the protrusion 32 (not shown in FIG. 8) engages the distal facing surface 15 of the plunger 14. Alternatively, further embodiments of the array advancing device 10 may employ a combination of an axially loading distal housing section 26, as illustrated in FIG. 8, and a two-piece hinged assembly for the proximal housing section, as shown in FIG. 6A.

Figure 9A:
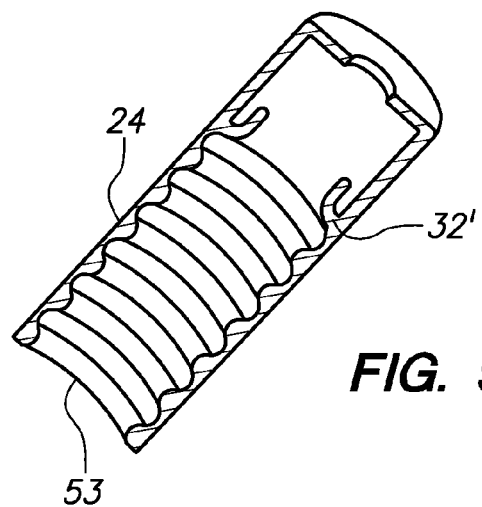
FIGS. 9A-C are cross sectional views of yet another alternative embodiment of the proximal housing section, depicting an annular protrusion.
Figure 9B:
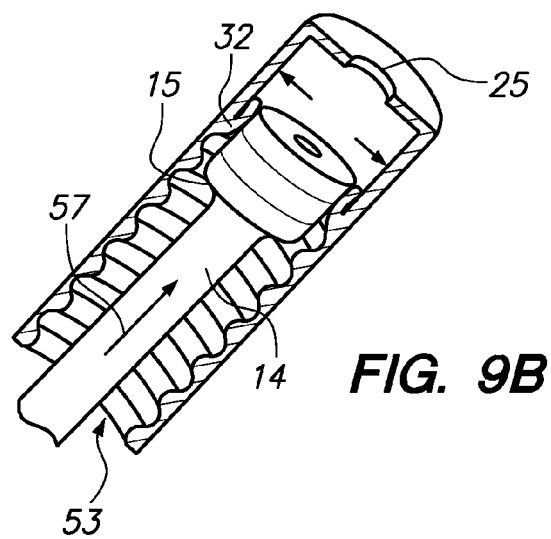
Figure 9C:
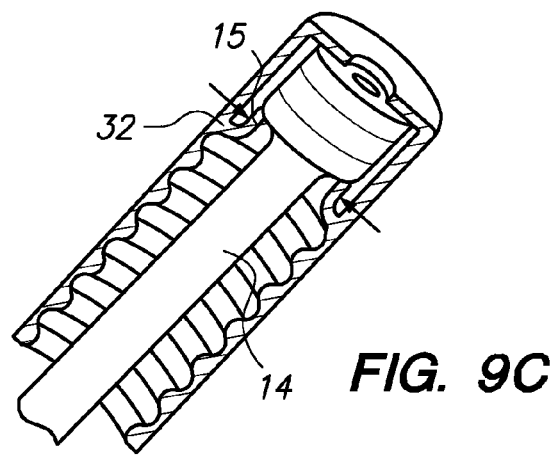

FIGS. 9A-C, depict an alternative embodiment of the annual protrusion, referred to as 32', of the proximal housing section 24, which comprises a flexible resilient material that depresses when the ablation probe plunger 14 is being axially received into a distal end opening 53 of the proximal housing section 24 (indicated by arrow 57 in FIG. 9B), and is self-restoring, as shown in FIG. 9C, to cooperatively engage the distal facing surface 15 of the plunger 14 when the plunger 14 is positioned into the proximal housing section 24.

The forgoing illustrated and described embodiments of the invention are susceptible to various modifications and alternative forms, and it should be understood that the invention generally, as well as the specific embodiments described herein, are not limited to the particular forms or methods disclosed, but to the contrary cover all modifications, equivalents and alternatives falling within the scope of the appended claims.

What is claimed is:

1. An array advancing system comprising:
   an ablation probe, the ablation probe comprising an array of electrode elements deployable from a distal portion or an elongate delivery cannula, a handle connected to a proximal portion of the delivery cannula, and a plunger coupled in a reciprocating fashion to the handle, the plunger coupled to the electrode array elements such that, when the plunger is extended proximally relative to the handle, the electrode elements are moved into the cannula, and when the plunger is depressed distally into the handle, the electrode elements are moved out of the cannula; and
   a separate array advancing device detachable from the ablation probe comprising a housing sized for receiving the probe handle and plunger of the ablation probe, the housing having a proximal section configured to engage the plunger, and a distal section configured to engage the handle, the proximal housing section being controllably moveable relative to the distal housing section, wherein the proximal and distal housing are detachably coupled to one another, and wherein the distal housing comprises a first hinged assembly and the proximal housing comprises a second hinged assembly, and wherein the proximal housing section is threadably coupled to the distal housing section.

2. The array advancing system of claim 1, wherein the proximal housing section is controllably movable relative to the distal housing section by rotating the proximal housing section relative to the distal housing section.

3. The array advancing system of claim 2, wherein, when the ablation probe handle and plunger are positioned in the housing, rotation of the proximal housing section relative to the distal housing section in a first direction depresses the plunger into the handle, and rotation of the proximal housing section relative to the distal housing section in a second direction extends the plunger proximally relative to the handle.

4. The array advancing system of claim 3, wherein the proximal housing section comprises a protrusion extending radially inward and sized to cooperatively engage a distal facing surface of the ablation probe plunger for causing the plunger to be extended proximally relative to the handle upon rotation of the of the proximal housing section in the second direction relative to the distal housing section.

5. The array advancing system of claim 1, further comprising a drive device configured to control movement of the proximal housing section relative to the distal housing section.

6. The array advancing system of claim 1, wherein the proximal housing section comprises two adjacent open portions joined by the second hinged assembly.

7. The array advancing system of claim 6, the two adjacent open potions comprising one or more pairs of snap fittings.

8. The array advancing system of claim 1, wherein the distal housing section comprises two adjacent open portions joined by the first hinged assembly.

9. The array advancing system of claim 8, the two adjacent open potions comprising one or more pairs of snap fittings.

10. An array advancing system comprising:
  an ablation probe comprising an array of electrode elements deployable from a distal portion of an elongate delivery cannula, a handle connected to a proximal portion of the delivery cannula, and a plunger coupled in a reciprocating fashion to the handle, the plunger coupled to the electrode array elements such that, when the plunger is extended proximally relative to the handle, the electrode elements are withdrawn into the cannula, and when the plunger is depressed distally into the handle, the electrode elements are deployed out of the cannula; and
  a separate array advancing device detachable from the ablation probe comprising a housing sized for receiving the probe handle and plunger of the ablation probe, the housing having a proximal section configured to engage the plunger, and a distal section configured to engage the handle, the proximal housing section being controllably moveable relative to the distal housing section, wherein the proximal and distal housing are fixedly coupled to one another and wherein the proximal housing section includes are releasably-secured retention member disposed over a proximal housing end opening configured for axially loading the ablation probe therethrough.

11. The array advancing system of claim 10, wherein the proximal housing section is controllably movable relative to the distal housing section by rotating the proximal housing section relative to the distal housing section.

12. The array advancing system of claim 11, wherein, wherein the ablation probe handle and plunger are positioned in the housing, rotation of the proximal housing section relative to the distal housing section in a first direction depresses the plunger into the handle, and rotation of the proximal housing section relative to the distal housing section in a second direction extends the plunger proximally relative to the handle.

13. The array advancing system of claim 12, wherein the proximal housing section comprises a protrusion extending radially inward and sized to cooperatively engage a distal facing surface of the ablation probe plunger for causing the plunger to be extended proximally relative to the handle upon rotation of the of the proximal housing section in the second direction relative to the distal housing section.

14. The array advancing system of claim 10, further comprising a drive configured to control movement of the proximal housing section relative to the distal housing section.

15. The array advancing system of claim 10, wherein the proximal housing section is threadably coupled to the distal housing section.

* * * * *